United States Patent
Rogel

[11] Patent Number: 6,076,003
[45] Date of Patent: Jun. 13, 2000

[54] ELECTROCARDIOGRAPHY ELECTRODES HOLDER AND MONITORING SET

[75] Inventor: Dan Rogel, Haifa, Israel

[73] Assignee: R.Z. Comparative Diagnostics Ltd., Haifa, Israel

[21] Appl. No.: 09/071,738

[22] Filed: May 1, 1998

[51] Int. Cl.[7] .................................................. A61B 5/0408
[52] U.S. Cl. ............................................................ 600/390
[58] Field of Search .................................. 600/382, 388, 600/389, 390, 393

[56] References Cited

U.S. PATENT DOCUMENTS

| | | | |
|---|---|---|---|
| D. 313,652 | 1/1991 | Lavine . | |
| 4,328,814 | 5/1982 | Arkans . | |
| 4,353,372 | 10/1982 | Ayer | 600/393 |
| 4,583,549 | 4/1986 | Manoli . | |
| 4,763,660 | 8/1988 | Kroll et al. . | |
| 4,852,572 | 8/1989 | Nakahashi et al. . | |
| 5,007,427 | 4/1991 | Suzuki et al. | 600/389 |
| 5,042,481 | 8/1991 | Suzuki et al. . | |
| 5,327,888 | 7/1994 | Imram . | |
| 5,341,806 | 8/1994 | Gadsby et al. . | |
| 5,507,290 | 4/1996 | Kelly et al. . | |

Primary Examiner—William E. Kamm
Attorney, Agent, or Firm—Mark M. Friedman

[57] ABSTRACT

An electrocardiography electrodes holder featuring (a) a flexible nonconductive flattened body having a fixed precordial configuration, the body featuring a first plane and an opposite second plane; (b) six electrocardiography electrode accepting holes formed in the flexible nonconductive flattened body traversing the planes for respectively engaging six electrocardiography electrodes, each of the six electrode accepting holes featuring a conductive inner circumference, the electrode accepting holes being located in a predetermined pattern effective for the precordial electrocardiography recordings; (c) six conductive recording lines electrically communicating with the conductive inner circumference of the six electrode accepting holes, the six conductive lines being on the second plane of the flexible nonconductive flattened body; (d) a first set of six conductive grounding lines, each being associated with one of the six conductive recording lines for electrically shielding the six conductive recording lines; (e) at least one terminal for electrically connecting the six conductive recording lines to a cardiometer and for grounding the conductive grounding lines. The electrocardiography electrodes holder can be a part of a set further including electrocardiography electrodes, a holding strap and a cardiometer.

24 Claims, 4 Drawing Sheets

ELECTROCARDIOGRAPHY ELECTRODES HOLDER AND MONITORING SET

FIELD AND BACKGROUND OF THE INVENTION

The present invention relates to an electrocardiography electrodes holder used to monitor and record the electrical activity produced by the human heart and, more particularly, to a holder for accepting electrodes useful in electrocardiography (ECG).

The electrical potential generated by the heart appears throughout the body and on the surface of the body. Such electrical potentials are helpful to physicians in evaluating the heart's condition. Six basic leads, I, II, III, AVR, AVF and AVL, make up the frontal plane ECG. These are derived from the various permutations of pairs of electrodes with one electrode located on the right arm, one located on the left arm, and two located on the legs.

When physicians examine the ECG in the transverse plane, they utilize chest leads. In this procedure, electrodes are placed at various anatomically defined positions on the chest wall, and are connected to a cardiometer (ECG monitor and/or recorder). These leads are known as precordial ECG leads.

The position of these precordial lead electrodes, designated V1 through V6, is as follows: V1 is located on the fourth intercostal space at the right sternal margin; V2 is located on the fourth intercostal space at the left sternal margin; V3 is located midway between electrode V2 and electrode V4; electrode V4 is located on the fifth intercostal space at the mid-clavicular line; electrode V5 is located on the same level as electrode V4 and on an anterior axillary line; and electrode V6 is located on the same level as electrode V4 and on a mid-axillary line.

Because the surface of the heart is in close proximity to the chest wall, each precordial electrode and its accompanying lead primarily records the electrical activity or potential of the cardiac musculature immediately beneath the electrode's position. Therefore, to achieve proper results, the medical technician, particularly when measuring precordial ECG, must be careful to place each chest electrode at its precise location on the chest.

When using individual electrodes, this procedure can prove to be inconvenient, time consuming and sometimes inaccurate. Furthermore, if for some reason a precordial ECG recording has to be repeated on the same patient, the probability of locating individual electrodes at the same position is slight.

For at risk individuals which preferably periodically conduct self ECG testing at home and/or for individuals under actual pain this task is altogether impossible.

U.S. Pat. Nos. 4,328,814 and 5,341,806 discloses an ECG strip in which individual electrodes are physically connected to one another through bundled conductors terminating in a connector block. Although perhaps more convenient than separate electrodes, this invention also requires a medical technician to individually place each of the electrodes on the body of the patient, thereby consuming valuable time and making repeatability of measurement subject to inaccuracies because of improper placement. The bundling of conductors in these invention does not materially improve positioning of the electrodes, as each must be individually placed onto the patient's chest.

U.S. Pat. No. 4,583,549, teaches an ECG electrode pad comprising a flexible non-conductive pad with a plurality of ECG electrodes positioned thereon to correspond with the anatomically correct placement for precordial ECG electrodes to be utilized in electrocardiographic monitoring or recording.

Other related art is disclosed in U.S. Pat. No. 5,507,290; D0313,652; U.S. Pat. Nos. 5,327,888; 5,042,481; 4,852,572; and 4,763,660. The devices disclosed in these U.S. patents suffer one or more limitations, such as, lack of precise repositioning ability, failure to intimately follow chest curvatures and/or cross talk between ECG leads. These devices are at all not applicable for self ECG testing.

There is thus a widely recognized need for, and it would be highly advantageous to have, a an electrocardiography electrodes holder devoid of the above limitations.

SUMMARY OF THE INVENTION

According to the present invention there is provided an electrocardiography electrodes holder and an electrocardiography monitoring set including same.

According to further features in preferred embodiments of the invention described below, the electrocardiography electrodes holder comprising (a) a flexible nonconductive flattened body having a fixed precordial configuration, the body featuring a first plane and an opposite second plane; (b) six electrocardiography electrode accepting holes formed in the flexible nonconductive flattened body traversing the planes for respectively engaging six electrocardiography electrodes, each of the six electrode accepting holes featuring a conductive inner circumference, the electrode accepting holes being located in a predetermined pattern effective for the precordial electrocardiography recordings; (c) six conductive recording lines electrically communicating with the conductive inner circumference of the six electrode accepting holes, the six conductive lines being on the second plane of the flexible nonconductive flattened body; (d) a first set of six conductive grounding lines, each being associated with one of the six conductive recording lines for electrically shielding the six conductive recording lines; (e) at least one terminal for electrically connecting the six conductive recording lines to a cardiometer and for grounding the conductive grounding lines.

According to still further features in the described preferred embodiments the first set of the six conductive grounding lines are on the second plane of the flexible nonconductive flattened body.

According to still further features in the described preferred embodiments the electrocardiography electrodes holder further comprising (f) a second set of six conductive grounding lines being on the first plane of the flexible nonconductive flattened body, each being associated with one of the six conductive recording lines for further electrically shielding the six conductive recording lines; and According to still further features in the described preferred embodiments the first set of six conductive grounding lines are on the first plane of the flexible nonconductive flattened body.

According to still further features in the described preferred embodiments the electrocardiography electrodes holder further comprising (f) a second set of six conductive grounding lines being on the second plane of the flexible nonconductive flattened body, each being associated with one of the six conductive recording lines for further electrically shielding the six conductive recording lines.

According to still further features in the described preferred embodiments at least one, preferably both the first and second planes are laminated with a non-conductive laminate.

According to still further features in the described preferred embodiments designed such that when the holder is used for the precordial electrocardiography recordings the first plane faces a chest of a user.

According to still further features in the described preferred embodiments the predetermined pattern effective for the precordial electrocardiography recordings includes two of the electrode accepting holes equidistantly positioned on opposite sides of a user's sternum, whereas the four remaining electrode accepting holes are located at predetermined locations relative to the two electrode accepting holes in an anatomically correct placement for sensing precordial electrocardiography signals from the user's body, at locations corresponding to a first location at a fifth intercostal space along the mid-clavicular line, to a second location about mid-way between the first location and an adjacent one of the two holes, to a third location on an anterior axillary line, and to a fourth location on a mid-axillary line.

According to still further features in the described preferred embodiments the conductive grounding lines are on the second plane, whereas each of the six conductive grounding lines of the first set of six conductive grounding lines features a path that surrounds its respective electrode accepting hole and conductive recording line.

According to still further features in the described preferred embodiments the conductive grounding lines are on the first plane, whereas each of the six conductive grounding lines of the first set of six conductive grounding lines features a path that surrounds its respective electrode accepting hole and comigrates along its respective conductive recording line.

According to still further features in the described preferred embodiments all of the conductive grounding lines are in electrical communication.

According to still further features in the described preferred embodiments the at least one terminal is a seven pins plug, six of the pins respectively communicate with the six conductive recording lines, whereas the seventh pin communicates with all of the conductive grounding lines.

According to still further features in the described preferred embodiments the holder is formed as a printed circuit board, whereas all of the conductive lines are printed thereon.

According to still further features in the described preferred embodiments the holder is of a thickness of between about 0.05 and about 0.5 millimeters.

According to still further features in the described preferred embodiments the holder is of a thickness of between about 0.1 and about 0.2 millimeters.

According to still further features in the described preferred embodiments the holder is made of a glass-epoxy substance.

According to still further features in the described preferred embodiments each of the electrode accepting holes is designed for tightly holding its respective electrocardiography electrode, while at the same time for permitting angular freedom of its respective electrocardiography electrode, so as to allow an improved contact between each of the electrocardiography electrodes and the chest of the user when the holder is in use.

According to still further features in the described preferred embodiments each of the electrode accepting holes features a first width and is designed for accepting its respective electrode which features a second width larger than the first width, each of the electrode accepting holes therefore features a plurality of outwardly extending cuts which form spring-like bendable elements therebetween surrounding the hole, for permitting the tight hold of the respective electrocardiography electrode, while at the same time for permitting angular freedom of the respective electrocardiography electrode.

According to still further features in the described preferred embodiments the electrocardiography electrodes holder further comprising at least one positioning element for accurate repetitive positioning of the holder with respect to the chest of the user.

According to still further features in the described preferred embodiments the at least on positioning element includes a neck positioner.

According to still further features in the described preferred embodiments the at least one positioning element includes an arm pit positioner.

According to still further features in the described preferred embodiments the at least one positioning element is detachably connectable to the holder.

According to still further features in the described preferred embodiments there is provided an electrocardiography monitoring set comprising (a) an electrocardiography electrodes holder according to any of its embodiments and at least one of the following: a stretchable strap having connecting ends for holding the holder after being accurately positioned on the chest of the user; a plurality of electrocardiography electrodes; and a cardiometer.

The present invention successfully addresses the shortcomings of the presently known configurations by providing an electrocardiography electrodes holder designed to enable self electrocardiography monitoring, the holder features (i) improved electrical shielding of the electrical components employed, thereby reducing or elimination adverse effects associated with cross talk and external electromagnetic disturbances, (ii) means for accurate and repetitive self positioning of precordial electrocardiography electrodes over a chest of a user, (iii) means of ensuring improved electrical contact between the precordial electrocardiography electrodes and the chest of the user, and (iv) compatibility with a variety of electrocardiography electrodes and cardiometers.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1A:
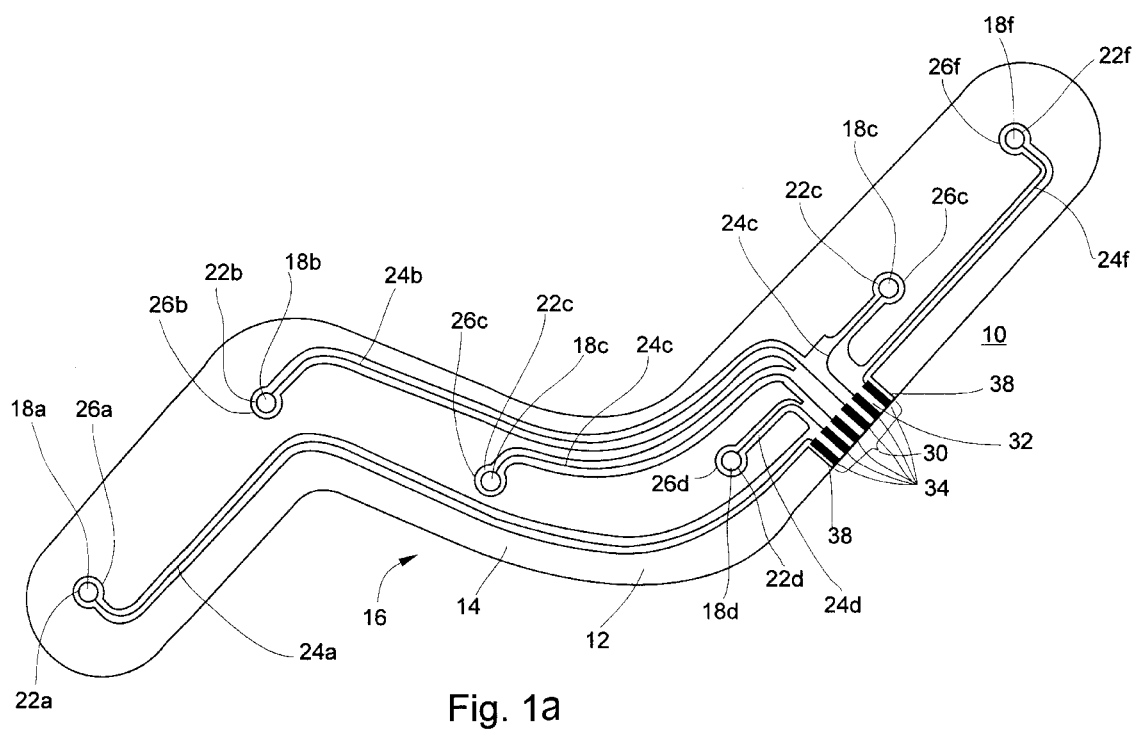
FIGS. 1a and 1b are top views of both sides of an electrocardiography electrodes holder according to the present invention.

The present invention is of an electrocardiography electrodes holder which can be used to hold electrodes useful in monitoring and recording the electrical activity produced by the human heart. Specifically, the present invention is designed for operation by the user him/herself for self electrocardiography monitoring.

The purpose of the present invention is to provide an electrocardiography electrodes holder that is inexpensive, convenient and easy to use by the user him/herself or by medical personnel, and that allows for a high probability of proper placement of the electrodes on the user and for easy repeatability of recordings.

The principles and operation of an electrocardiography electrodes holder according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
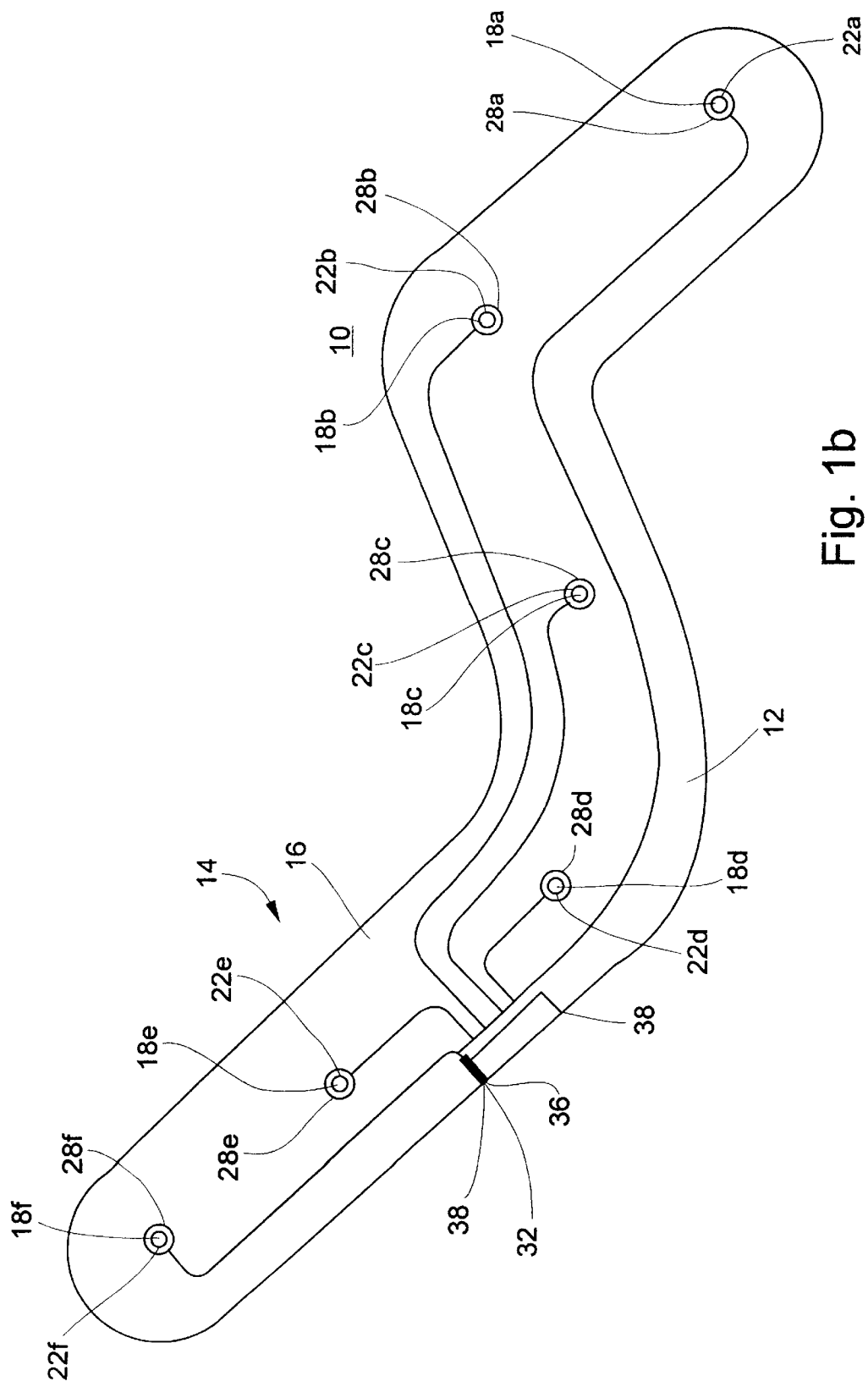

Referring now to the drawings, FIGS. 1a–b illustrate the electrocardiography electrodes holder according to the present invention, which is referred to hereinbelow as electrocardiography electrodes holder 10, or simply holder 10.

Electrocardiography electrodes holder 10 includes a flexible nonconductive flattened body 12 featuring a fixed precordial configuration as further detailed hereinunder. Body 12 features a first plane 16, shown in FIG. 1b, and an opposite second plane 14, shown in FIG. 1a.

Considering the range of sizes of individuals it is envisioned that the great percentage of all patients/users can be tested by the use of three to four different holder sizes, namely pediatric, medium size, adult size and large adult size.

Figure 2:
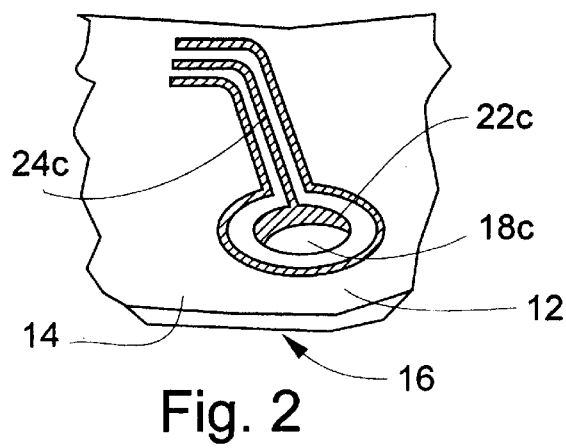
FIG. 2 is a partial perspective view of the electrocardiography electrodes holder according to the present invention, showing a single electrocardiography electrode accepting hole.
Figure 3:
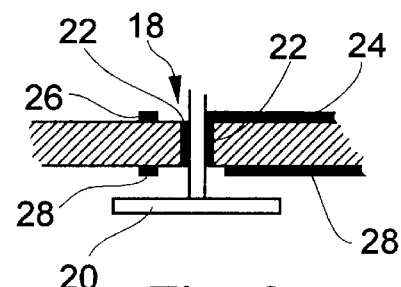
FIG. 3 is a partial cross sectional view of the electrocardiography electrodes holder according to the present invention, showing a single electrocardiography electrode accepting hole.

Electrocardiography electrodes holder 10 further includes six electrocardiography electrode accepting holes 18a–f formed in flexible nonconductive flattened body 12, traversing planes 14 and 16, for respectively engaging six electrocardiography electrodes 20 (FIG. 3). FIG. 2 shows a perspective view of a single electrode accepting hole 18. FIG. 3 shows a sectional view of a single electrode accepting hole 18 engaged by an electrode 20. Each of electrode accepting holes 18a–f features a conductive inner circumference 22a–f, respectively, designed to be in electrical contact with its respective electrode 20. As further detailed below, electrode accepting holes 18a–f are located in a predetermined pattern effective for precordial electrocardiography recordings.

Electrocardiography electrodes holder 10 further includes six conductive recording lines 24a–f. Each of lines 24a–f is in electrical communication with a respective conductive inner circumference 22a–f of one of electrode accepting holes 18a–f. Conductive lines 24a–f are on second plane 14 of flexible nonconductive flattened body 12.

As best seen in FIG. 1a, electrocardiography electrodes holder 10 further includes a first set of six conductive grounding lines 26a–f. Lines 26a–f are on second plane 14 of flexible nonconductive flattened body 12 and each of them is associated with, yet electrically insulated from, one of conductive recording lines 24a–f, respectively, for electrically shielding conductive recording lines 24a–f.

As best seen in FIG. 1b, electrocardiography electrodes holder 10 further includes a second set of six conductive grounding lines 28a–f. Lines 28a–f are on first plane 16 of flexible nonconductive flattened body 12. Each of lines 28a–f is associated with, yet electrically insulated from, one of conductive recording lines 24a–f, respectively, for electrically shielding conductive recording lines 24a–f.

As best seen in FIG. 1a, electrocardiography electrodes holder 10 further includes at least one terminal 30 for electrically connecting each of conductive recording lines 24a–f to a cardiometer and for grounding conductive grounding lines 26a–f and 28a–f.

Figure 4:
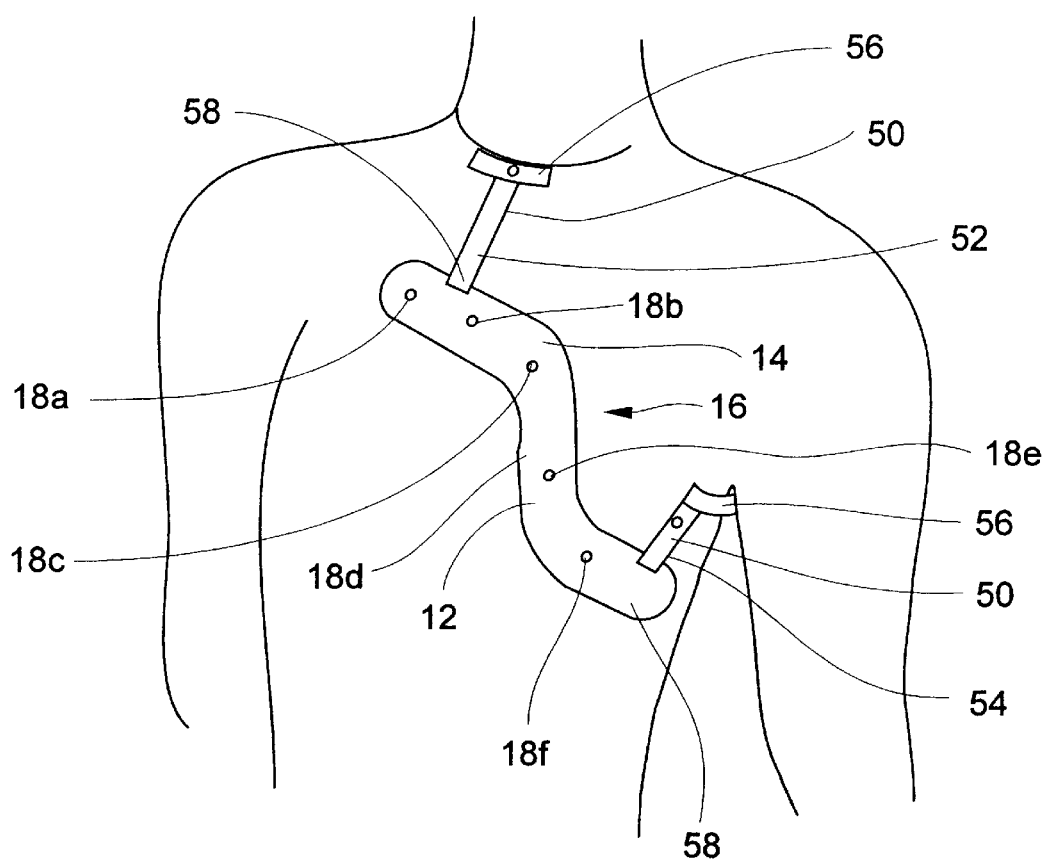
FIG. 4 shows the electrocardiography electrodes holder according to the present invention when used, it further shows positioners employed for accurate self positioning thereof with respect to the chest of the user.

According to a preferred embodiment of the present invention and as specifically shown in FIG. 4, electrocardiography electrodes holder 10 is designed such that when holder 10 is used for precordial electrocardiography recordings, first plane 16 faces the chest of the user, whereas second plane 16, faces the atmosphere.

According to another preferred embodiment of the present invention, at least one, preferably both of first 16 and second 14 planes are laminated (except for holes 18) with a nonconductive laminate, so as to electrically insulate lines 24, 26 and/or 28 from the body and the atmosphere.

The predetermined pattern effective for precordial electrocardiography recordings is described herein with respect to FIG. 4.

Hole 18a is designed to accept a V1 electrocardiography electrode and is shown in its proper location on the forth intercostal space at the right sternal margin. Hole 18b is designed to accept a V2 electrocardiography electrode and is shown at the fourth intercostal space at the left sternal margin. Holes 18a and 18b lie equidistant from the user's sternum. Hole 18c is designed to accept a V3 electrocardiography electrode and is shown midway between holes 18b and hole 18d which is designed to accept a V4 electrocardiography electrode. Hole 18d is located on the fifth intercostal space at a mid-clavicular line. Hole 18e is designed to accept a V5 electrocardiography electrode and is located on the same horizontal level as hole 18d and on an anterior axillary line. Hole 18f is designed to accept a V6 electrocardiography electrode and is located also on the same horizontal level as hole 18d and is on a mid-axillary line.

According to a preferred embodiment of the present invention each of conductive grounding lines 26a–f features a path that surrounds its respective electrode accepting hole 18a–f and conductive recording line 24a–f.

According to another preferred embodiment of the present invention each of conductive grounding lines 28a–f features a path that surrounds its respective electrode accepting hole 18a–f and comigrates along its respective conductive recording line 24a–f.

When both configurations are used, the result is that lines 24a–f are best shielded both from cross talk thereamongst and from external electromagnetic disturbances.

In a preferred embodiment of the invention, all of conductive grounding lines 26a–f and 28a–f are in electrical communication. In another preferred embodiment terminal 30 is a seven pins plug 32, six of the pins 34 (FIG. 1a) respectively communicate with conductive recording lines 24a–f, whereas the seventh pin 36 (FIG. 1b) communicates with all of conductive grounding lines 26a–f and 28a–f. Pin 36 is shown, in a non-limiting fashion, to be located on first plane 16 of body 12. In this case, grounding lines 26a–f which are arranged on plane 14, should traverse body 12 to its other plane 16 and connect to pin 36. Traversing can be effected via an additional hole formed in body 12 (not shown), or alternatively, over the circumference of body 12, at any location such as locations 38.

Holder 10 is preferably formed as a printed circuit board, whereas all of conductive lines 24a–f, 26a–f and 28a–f are printed thereon. According to preferred embodiments of the invention as described herein both sides of the printed circuit board are printed. To achieve a desired level of flexibility, holder 10 preferably features a thickness of between about 0.05 and about 0.5 millimeters, more preferably of between about 0.1 and about 0.2 millimeters. It will be appreciated by one ordinarily skilled in the art that double sided printed circuit boards, e.g., glass-epoxy substance based printed circuit boards, of the above thickness ranges are readily manufacturable.

Figure 5:
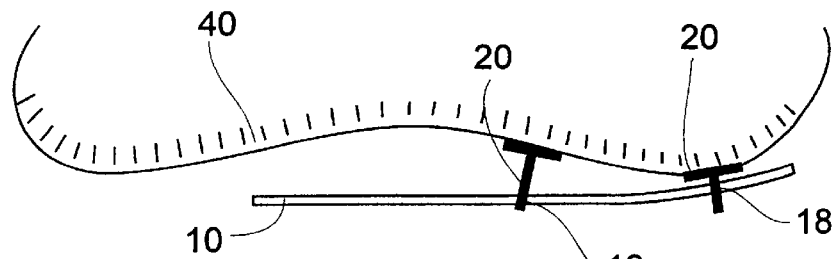
FIG. 5 is a cross section view of a chest and of the electrocardiography electrodes holder according to the present invention, demonstrating difficulties arising due to the chest's curvatures in achieving intimate electrical contact between the body of the user and the electrocardiography electrodes.

As shown in FIG. 5, a typical chest 40 features unique curvatures. Therefore, according to a preferred embodiment of the present invention, each of electrode accepting holes 18 is designed for tightly holding its respective electrocardiography electrode 20, while at the same time permitting angular freedom of its respective electrocardiography electrode 20, so as to allow an improved contact between each of electrocardiography electrodes 20 and the chest 40 of the user when holder 10 is in use.

Figures 6, 7:
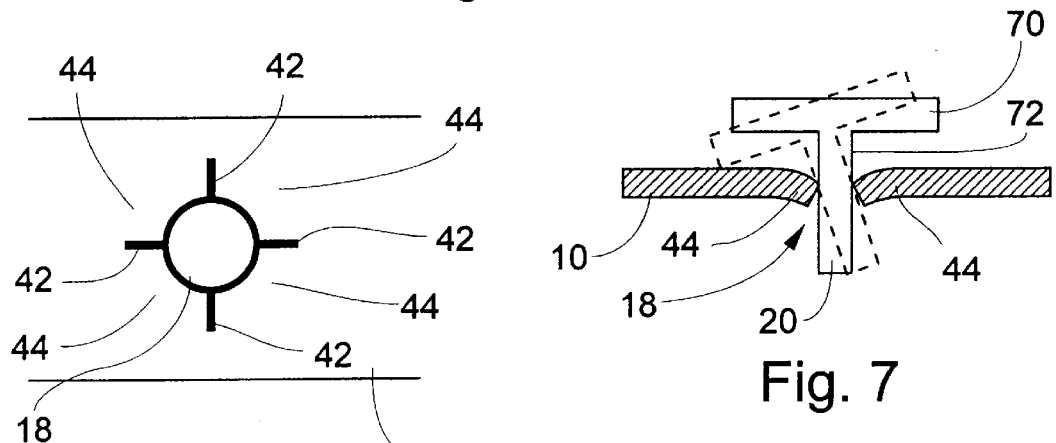
FIG. 6 is a top view of an electrocardiography electrode accepting hole formed in the electrocardiography electrodes holder according to the present invention.
FIG. 7 is a cross sectional view of an electrocardiography electrode accepting hole formed in the electrocardiography electrodes holder according to the present invention, shown engaged by an electrocardiography electrode.

This is preferably accomplished as described in FIGS. 6–7. Each of electrode accepting holes 18 features a plurality of outwardly extending (e.g., radial) cuts 42 which form spring-like bendable elements 44 therebetween, surrounding hole 18, for permitting tight hold of a respective electrocardiography electrode 20, while at the same time for permitting angular freedom of the respective electrocardiography electrode 20, such that each of electrodes 20 may be easily contacted with the chest of the user, as shown in FIG. 5. The diameter of holes 18 in this case is selected smaller than the diameter of the stems of electrodes 20, such that by inserting the stem of electrode 20 through its respective hole 18, elements 44 bend, as shown in FIG. 6, to enable the above described preferred features.

Referring again to FIG. 4, according to a preferred embodiment of the present invention, electrocardiography electrodes holder 10 further includes at least one positioning element 50 for accurate repetitive positioning of holder 10 with respect to the chest of the user, even when self attempted.

FIG. 4 shows two different positioning elements 50, both are preferably provided with holder 10. One positioning element 50 is preferably a neck positioner 52, whereas the other is preferably an arm pit positioner 54. Positioners 50 are designed to have their distal ends 56 positioned in predefined and easy to locate positions in the human body, such as under the circoid and/or the arm pit. At their proximal ends 58, positioners 50 are connectable to, or integrally formed with, body 12 of holder 10. Connecting positioners 50 to body 12 may be effected via connecting surfaces one with tiny hooks and the other with a dense pile, that interlock when pressed together, such as, but not limited to, VELCRO, to insure easy assembly/disassembly. Positioners 50 are preferably provided in different sizes so as to fit users of different sizes.

Figure 8:
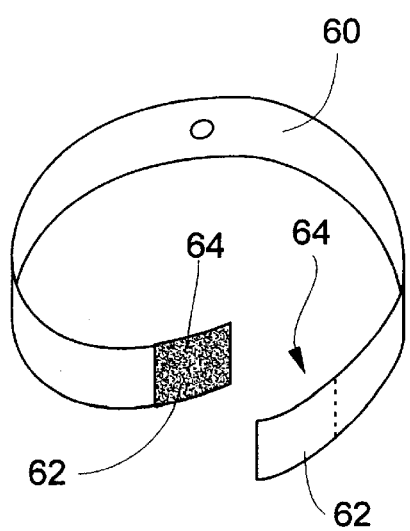
FIG. 8 is a perspective view of a stretchable strap employed for holding the electrocardiography electrodes holder according to the present invention in place after its accurate positioning and during electrocardiography recording.

As shown in FIG. 8, the electrocardiography electrodes holder according to the present invention is preferably provided with a stretchable strap 60 having fastening ends 62 for holding holder 10 in position after being accurately positioned on the chest of the user. Strap 60 is provided in different lengths and is preferably length adjustable, so as to be applicable and/or adjustable to users of different sizes. After the accurate positioning of holder 10, strap 60 is fastened around the user's body at the chest level, so as to hold in place holder 10 during the precordial electrocardiography test. Fastening ends 62 of strap 60 preferably include connecting surfaces 64 one with tiny hooks and the other with a dense pile, that interlock when pressed together, such as, but not limited to, VELCRO, to ensure its simple fastening and unfastening.

The precordial electrocardiography electrodes to be used with the electrocardiography electrodes holder according to the present invention may be of a standard type.

As shown in FIG. 7, for example, such an electrode 20 typically includes a disc 70 and a stem 72, both are made of a conductive material. Disc 72 is preferably a silver-plated copper disc and is designed to be in contact with the patient's body. Stem 72 is preferably a silver-plated copper stem. For better electrical contact with the user's body, such electrodes 20 can be coated with a pressure sensitive hypoallergenic adhesive, as well known in the art, or alternatively they can be used with a conductive lubricant.

Figure 9:
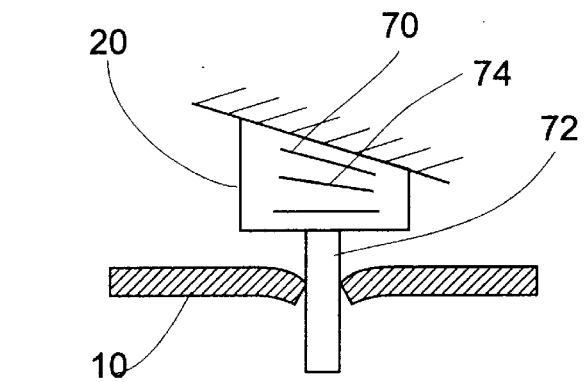
FIG. 9 is a cross sectional view of an electrocardiography electrode suitable for use with the electrocardiography electrodes holder according to the present invention.

As shown in FIG. 9, according to a preferred embodiment of the present invention disc 70 of electrodes 20 includes, or is made of, a compressible conductive material 74, such as, but not limited to, commercial conductive rubber, which enables improved electrical contact with the user's body, especially in regions featuring curvatures.

Suitable standard precordial electrodes compatible with the electrocardiography electrodes holder according to the present invention are available from Promedico, Compea and many other companies.

The present invention can be used with any standard cardiometer connectable to the V1–V6 precordial leads. Suitable standard cardiometers compatible with the electrocardiography electrodes holder according to the present invention are available from any manufacturer of commercial ECG cardiometer units.

However, as emphasized throughout the specification, the electrocardiography electrodes holder of the present invention is especially adapted for self electrocardiography testing. Therefore, according to a prefered embodiment it is used in combination with a self operable cardiometer which also provides analysis of the results.

A suitable self operable cardiometer is described in U.S. Pat. application Ser. No. 08/914,808, which is incorporated by reference as if fully set forth herein, and discloses a device and method for self electrocardiography monitoring and real time analysis thereof. The device includes (a) a sensing element and a processing element for recording and storing a first ECG signal from a user during a first time interval and recording a second ECG signal from the same user during a second time interval; (b) a comparing element for comparing the second ECG signal to the first ECG signal; and (c) a logical decision element for making a logical decision based on the comparison and providing a recommendation to the user of a step he should take.

Figure 10:
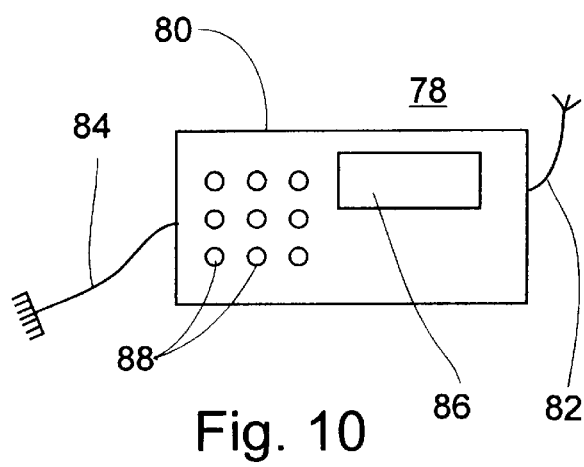
FIG. 10. is a schematic depiction of a cardiometer suitable for use with the electrocardiography electrodes holder according to the present invention.

FIG. 10 schematically presents a cardiometer 78 which includes a housing 80 for housing the electronic components thereof, a cord 84 for communicating with terminal 30 of holder 10 (FIGS. 1*a–b*), a display 86 for providing the user with information, and operation and control buttons 88 for operating and controlling cardiometer 78.

The present invention provides numerous advantages as is compared with the prior art. First, the present invention provides a holder designed to enable self electrocardiography monitoring. Second, the present invention provides improved electrical shielding of the electrical components employed, thereby reducing or elimination adverse effects associated with cross talk and external electromagnetic disturbances. Third, the present invention provides means for accurate and repetitive self positioning of precordial electrocardiography electrodes over a chest of a user even following prolonged interval between adjacent measurements. Fourth, the present invention provides means of ensuring improved electrical contact between the precordial electrocardiography electrodes and the chest of the user. Finally, the present invention provides a diversified electrocardiography electrodes holder compatible with a variety of electrocardiography electrodes and a variety of cardiometers.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An electrocardiography electrodes holder comprising:
   (a) a flexible nonconductive flattened body having a fixed precordial configuration, said body featuring a first plane and an opposite second plane;
   (b) six electrocardiography electrode accepting holes formed in said flexible nonconductive flattened body traversing said first plane and said second plane for respectively engaging six electrocardiography electrodes, each of said six electrode accepting holes featuring a conductive inner circumference, said electrode accepting holes being located in a predetermined pattern on said flattened body, said predetermined pattern being effective for said precordial electrocardiography recordings;
   (c) six conductive recording lines electrically communicating with said conductive inner circumference of said six electrode accepting holes, said six conductive lines being on said second plane of said flexible nonconductive flattened body;
   (d) a first set of six conductive grounding lines, each one of said six conductive grounding lines electrically shielding one of said six conductive recording lines;
   (e) at least one terminal for electrically connecting said six conductive recording lines to a cardiometer and for grounding said conductive grounding lines.

2. The electrocardiography electrodes holder of claim 1, wherein said first set of said six conductive grounding lines are on said second plane of said flexible nonconductive flattened body.

3. The electrocardiography electrodes holder of claim 2, further comprising:
   (f) a second set of six conductive grounding lines being on said first plane of said flexible nonconductive flattened body, each one of said six conductive grounding lines of said second set serves for further electrically shielding one of said six conductive recording lines.

4. The electrocardiography electrodes holder of claim 1, wherein said first set of six conductive grounding lines are on said first plane of said flexible nonconductive flattened body.

5. The electrocardiography electrodes holder of claim 1, wherein the holder is designed, such that when the holder is used for said precordial electrocardiography recordings said first plane faces a chest of a user, such that said six conductive recording lines face away from the chest.

6. The electrocardiography electrodes holder of claim 1, wherein said predetermined pattern effective for said precordial electrocardiography recordings includes two of said electrode accepting holes equidistantly positionable on opposite sides of a user's sternum, whereas the four remaining electrode accepting holes are locatable at predetermined locations relative to said two electrode accepting holes in an anatomically correct placement for sensing precordial electrocardiography signals from said user's body, at locations correspondable to a first location at a fifth intercostal space along the mid-clavicular line, to a second location about mid-way between said first location and an adjacent one of said two holes, to a third location on an anterior axillary line, and to a fourth location on a mid-axillary line.

7. The electrocardiography electrodes holder of claim 1, wherein said conductive grounding lines are on said second plane, whereas each of said six conductive grounding lines of said first set of six conductive grounding lines features a path that surrounds its respective electrode accepting hole and conductive recording line.

8. The electrocardiography electrodes holder of claim 1, wherein said conductive grounding lines are on said first plane, whereas each of said six conductive grounding lines of said first set of six conductive grounding lines surrounds its respective electrode accepting hole and comigrates along its respective conductive recording line.

9. The electrocardiography electrodes holder of claim 1, wherein all of said conductive grounding lines are in electrical communication.

10. The electrocardiography electrodes holder of claim 1, wherein said at least one terminal is a seven pins plug, six of said pins respectively communicate with said six conductive recording lines, whereas said seventh pin communicates with all of said conductive grounding lines.

11. The electrocardiography electrodes holder of claim 1, wherein the holder is formed as a printed circuit board, whereas all of said conductive lines are printed thereon.

12. The electrocardiography electrodes holder of claim 1, wherein the holder is of a thickness of between about 0.05 and about 0.5 millimeters.

13. The electrocardiography electrodes holder of claim 12, wherein the holder is of a thickness of between about 0.1 and about 0.2 millimeters.

14. The electrocardiography electrodes holder of claim 1, wherein the holder is made of a glass-epoxy substance.

15. The electrocardiography electrodes holder of claim 1, wherein each of said electrode accepting holes features a plurality of outwardly extending cuts which form spring-like bendable elements therebetween surrounding said hole.

16. The electrocardiography electrodes holder of claim 1, further comprising at least one positioning element for accurate repetitive positioning of the holder with respect to the chest of the user.

17. The electrocardiography electrodes holder of claim 16, wherein said at least on positioning element includes a neck positioner.

18. The electrocardiography electrodes holder of claim 17, wherein said at least one positioning element further includes an arm pit positioner.

19. The electrocardiography electrodes holder of claim 16, wherein said at least one positioning element includes an arm pit positioner.

20. The electrocardiography electrodes holder of claim 16, wherein said at least one positioning element is detachably connectable to the holder via a connector.

21. An electrocardiography monitoring set comprising:
   (a) an electrocardiography electrodes holder including:
      (i) a flexible nonconductive flattened body having a fixed precordial configuration, said body featuring a first plane and an opposite second plane;
      (ii) six electrocardiography electrode accepting holes formed in said flexible nonconductive flattened body traversing said first plane and said second plane for respectively engaging six electrocardiography electrodes, each of said six electrode accepting holes featuring a conductive inner circumference, said electrode accepting holes being located in a predetermined pattern on said flattened body, said predetermined pattern being effective for said precordial electrocardiography recordings;
      (iii) six conductive recording lines electrically communicating with said conductive inner circumference of said six electrode accepting holes, said six conductive lines being on said second plane of said flexible nonconductive flattened body;
      (iv) a first set of six conductive grounding lines, each one of said six conductive grounding lines electrically shielding one of said six conductive recording lines;
      (v) a second set of six conductive grounding lines being on said first plane of said flexible nonconductive flattened body, further electrically shielding said six conductive recording lines; and
      (vi) at least one terminal for electrically connecting said six conductive recording lines to a cardiometer and for grounding said conductive grounding lines; and
   (b) a plurality of electrocardiography electrodes engagable in said accepting holes.

22. The electrocardiography monitoring set of claim 21, further comprising:
   (c) a stretchable strap having connecting ends for holding the holder after being accurately positioned on the chest of the user.

23. The electrocardiography monitor set of claim 21, wherein said electrocardiography electrodes holder further includes at least one positioning element for accurate positioning repetitive of the holder with respect to the chest of the user.

24. The electrocardiography monitor set of claim 21, further comprising:
   (b) a cardiometer connectable to said plurality of electrodes electrocardiography electrodes for conducting electrocardiography.

* * * * *